United States Patent [19]
Tokuyasu et al.

[11] Patent Number: 5,955,320
[45] Date of Patent: Sep. 21, 1999

[54] METHOD FOR PRODUCING 2-ACETYLAMINO-4-O-(2-AMINO-2-DEOXY-β-D-GLUCOPYRANOSYL)-2-DEOXY-D-GLUCOSE AND ITS SALTS

[75] Inventors: Ken Tokuyasu; Hiroshi Ono, both of Tsukuba; Mayumi Kameyama, Abiko; Yutaka Mori; Shioka Hamamatsu, both of Tsuchiura; Kiyoshi Hayashi, Tsuchiura, all of Japan

[73] Assignee: Director of National Food Research Institute, Ministry of Agriculture, Forestry and Fisheries, Tsukuba, Japan

[21] Appl. No.: 08/900,820

[22] Filed: Jul. 25, 1997

[30] Foreign Application Priority Data

May 30, 1997 [JP] Japan ........................ 156092

[51] Int. Cl.$^6$ .................. C12P 19/26; C12P 19/12; C07H 3/04
[52] U.S. Cl. .................. 435/84; 435/72; 435/100; 536/123.13; 536/124
[58] Field of Search .................. 435/100, 84, 72; 536/123.13, 124

[56] References Cited

PUBLICATIONS

Tokuyasu et al, Biosci. Biotech. Biochem. 60(10):1598–1603 (1996).
John et al, Proc. Natl. Acad. Sci. 90:625–629.
K. Tokuyasu et al., *Chitin and Chitosan Research*, 3, No. 2, pp. 142–143 (1997).
Mitsutomi et al., "Action Pattern of *Aeromonas hydrophila* Chitinase on Partially N–Acetylated Chitosan", Agric. Biol. Chem. 54(4), pp. 871–877, (1990).

Tokuyasu et al., "Deacetylation of chitin oligosaccharides of dp 2–4 by chitin deacetylase from *Colletotrichum lindemuthianum*", Carbohydrate Research 303 (1997) pp. 353–358.

Tokuyasu et al., "Purification and Characterization of Extracellular Chitin Deacetylase from *Colletrotrichum lindemuthianum*", Biosci. Biotech. Biochem. 60 (10), pp. 1598–1603 (1996).

*Primary Examiner*—Francisco Prats
*Attorney, Agent, or Firm*—Frishauf, Holtz, Goodman, Langer & Chick, P.C.

[57] ABSTRACT

Di-N-acetyl-D-chitobiose, which is easily available as a chitin decomposate or a chemical reagent, is reacted with a microorganisms-derived deacetylase to produce 2-acetylamino-4-O-(2-amino-2-deoxy-β-D-glucopyranosyl)-2-deoxy-D-glucose of formula (1).

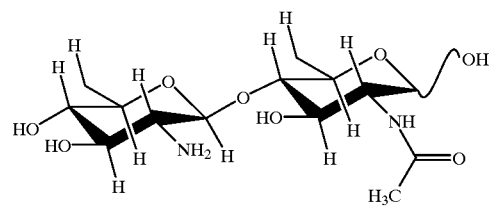

(1)

The method is quantitative and efficiently produces the compound (1). The compound (1) and its salts are usable as substrates for measuring enzymatic activities, and also as starting substances in the production of various food materials and in the field of glyco-chain engineering.

15 Claims, 4 Drawing Sheets

METHOD FOR PRODUCING 2-ACETYLAMINO-4-O-(2-AMINO-2-DEOXY-β-D-GLUCOPYRANOSYL)-2-DEOXY-D-GLUCOSE AND ITS SALTS

FIELD OF THE INVENTION

The present invention relates to a method for producing 2-acetylamino-4-O-(2-amino-2-deoxy-β-D-glucopyranosyl)-2-deoxy-D-glucose and its salts.

The compound is a partial hydrolysate of a natural substance, chitin, and therefore can be used as a substrate for measuring the activities of enzymes that decompose chitin-related compounds and also as a starting substance in the production of various food materials and in the field of glyco-chain engineering.

BACKGROUND OF THE INVENTION

Chitosan oligosaccharides which are prepared by hydrolyzing chitosan are widely used as edible ingredients essentially in the field of dietary supplements. The starting substance, chitosan generally has N-acetyl groups which partly remain in its sugar residues, and its hydrolysates, oligosaccharides generally have N-acetyl-D-glucosamine residues in addition to D-glucosamine residues.

Such partially-deacetylated chitin oligosaccharides have been reported to have an elicitor activity for plants and have an anticarious activity, and there are known some examples demonstrating that these activities of partially-deacetylated chitin oligosaccharides are higher than those of chitin oligosaccharides and chitosan oligosaccharides having the same degree of polymerization.

However, the substances which are referred to as partially-deacetylated chitin oligosaccharides are generally in the form of mixtures each comprising a plurality of different compounds, and their structures have not as yet been clarified. Therefore, it is very meaningful to provide partially-deacetylated chitin oligosaccharides each having a defined individual structure for the purpose of clarifying the mechanisms of chitin oligosaccharides, partially-deacetylated chitin oligosaccharides and chitosan oligosaccharides as to how they express their various physiological activities.

A report is known in which they say that 2-acetylamino-4-O-(2-amino-2-deoxy-β-D-glucopyranosyl)-2-deoxy-D-glucose which is the element unit of a partially-deacetylated chitin oligosaccharide having a defined structure can be produced by decomposing a partially-deacetylated polymer chitin with a chitinase (see Mitsutomi, M. et al., Agric. Biol. Chem., 54 (4) 871–877, 1990). In the reported method, however, hetero-oligosaccharides, of which their structures are very similar to the structure of said compound, are produced as side products along with said compound, and it is very difficult to isolate and purify said compound. For this reason, no one has heretofore tried to isolate said compound to use it as a glucide material in various fields.

SUMMARY OF THE INVENTION

The object of the present invention is to provide a method of almost quantitatively producing 2-acetylamino-4-O-(2-amino-2-deoxy-β-D-glucopyranosyl)-2-deoxy-D-glucose by reacting a substrate of di-N-acetyl-D-chitobiose, which is easily available as a chitin decomposate or a chemical reagent, with a microorganism-derived deacetylase.

Specifically, the present invention provides a method for producing 2-acetylamino-4-O-(2-amino-2-deoxy-β-D-glucopyranosyl)-2-deoxy-D-glucose of the following formula (1) and its acid-addition salts, which comprises reacting di-N-acetylchitobiose with a microorganism-derived deacetylase.

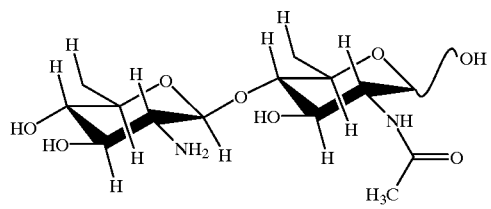

(1)

Salts of 2-acetylamino-4-O-(2-amino-2-deoxy-β-D-glucopyranosyl)-2-deoxy-D-glucose are typically acid-addition salts thereof (expressed with HX in the formula), which include, for example, hydrochlorides and acetates that may be represented by the following formula (2):

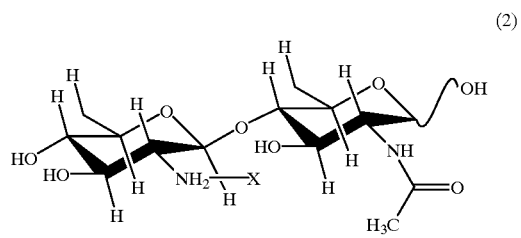

(2)

BRIEF DESCRIPTION OF THE DRAWINGS

FIG. 3A is a pattern of the sample as sampled just before the start of the reaction; FIG. 3B is a pattern of the sample as sampled in 15 minutes after the start of the reaction; FIG. 3C is a pattern of the sample as sampled in 30 minutes after the start of the reaction; and FIG. 3D is a pattern of the sample as sampled in 60 minutes after the start of the reaction.

FIG. 4A is a pattern of the sample as sampled in 90 minutes after the start of the reaction; FIG. 4B is a pattern of the sample as sampled in 120 minutes after the start of the reaction; FIG. 4C is a pattern of the sample as sampled in 150 minutes after the start of the reaction; and FIG. 4D is a pattern of the sample as sampled in 180 minutes after the start of the reaction.

DETAILED DESCRIPTION OF THE PREFERRED EMBODIMENTS

Now, the method of the present invention for producing 2-acetylamino-4-O-(2-amino-2-deoxy-β-D- glucopyranosyl)-2-deoxy-D-glucose and its acid-addition salts is described in detail hereinunder.

The starting material to be used in the method of the invention is di-N-acetylchitobiose. This is obtained easily as a decomposate of chitin, or is commercially available as a chemical reagent.

The microorganism-derived deacetylase must have the activity capable of predominantly removing the N-acetyl group existing in the N-acetyl-D-glucosamine residue positioned at the non-reducing terminal of di-N-acetylchitobiose. For example, it may be an imperfect fungi-derived chitin deacetylase, such as typically Colletotrichum lindemuthianum ATCC 56676-derived chitin deacetylase (see Biosci. Biotech. Biochem., 60 (10), 1598–1603, 1996).

This enzyme can be obtained, for example, as follows. The spores of the above-mentioned imperfect fungus are incubated in a liquid medium, and the active fraction is recovered from the culture. This can be directly used as a crude enzyme liquid, or may be purified in any ordinary manner to give a pure enzyme (see Japanese Patent Application Laid-Open No. 8-289785).

This enzyme is reacted with the starting compound, di-N-acetylchitobiose, whereby only the acetyl group of the N-acetylglucosamine residue positioned at the non-reducing terminal of said di-N-acetylchitobiose is removed to convert said residue to a glucosamine residue, thereby obtaining the intended product, 2-acetylamino-4-O-(2-amino-2-deoxy-β-D-glucopyranosyl)-2-deoxy-D-glucose.

Concretely, di-N-acetylchitobiose is dissolved in sodium tetraborate/HCl buffer (pH 8.5) to prepare a solution having a substrate concentration of from 0.1 to 0.5%, preferably about 0.2%.

To this solution is added from 0.01 to 0.3 units, preferably about 0.05 units of a microorganisms-derived chitin deacetylase, and reacted with said compound at from 30 to 60° C., preferably at 45° C., for from 1 to 6 hours, preferably from 2 to 4 hours.

Next, the reaction product is adsorbed by a cation-exchange resin, and the non-reacted compound is removed. Then, 0.1 N HCl is passed through the resin column, whereby the intended product is eluted. The cation-exchange resin to be used is preferably Amberlite CG-120 or the like.

If desired, a suitable acid, such as hydrochloric acid, acetic acid or the like, may be added to the thus-obtained product to prepare its salt.

The compound thus obtained according to the method of the present invention is essentially used as a substrate for measuring enzymatic activities and also as a starting substance in the production of various food materials and in the field of glyco-chain engineering.

Figure 1:
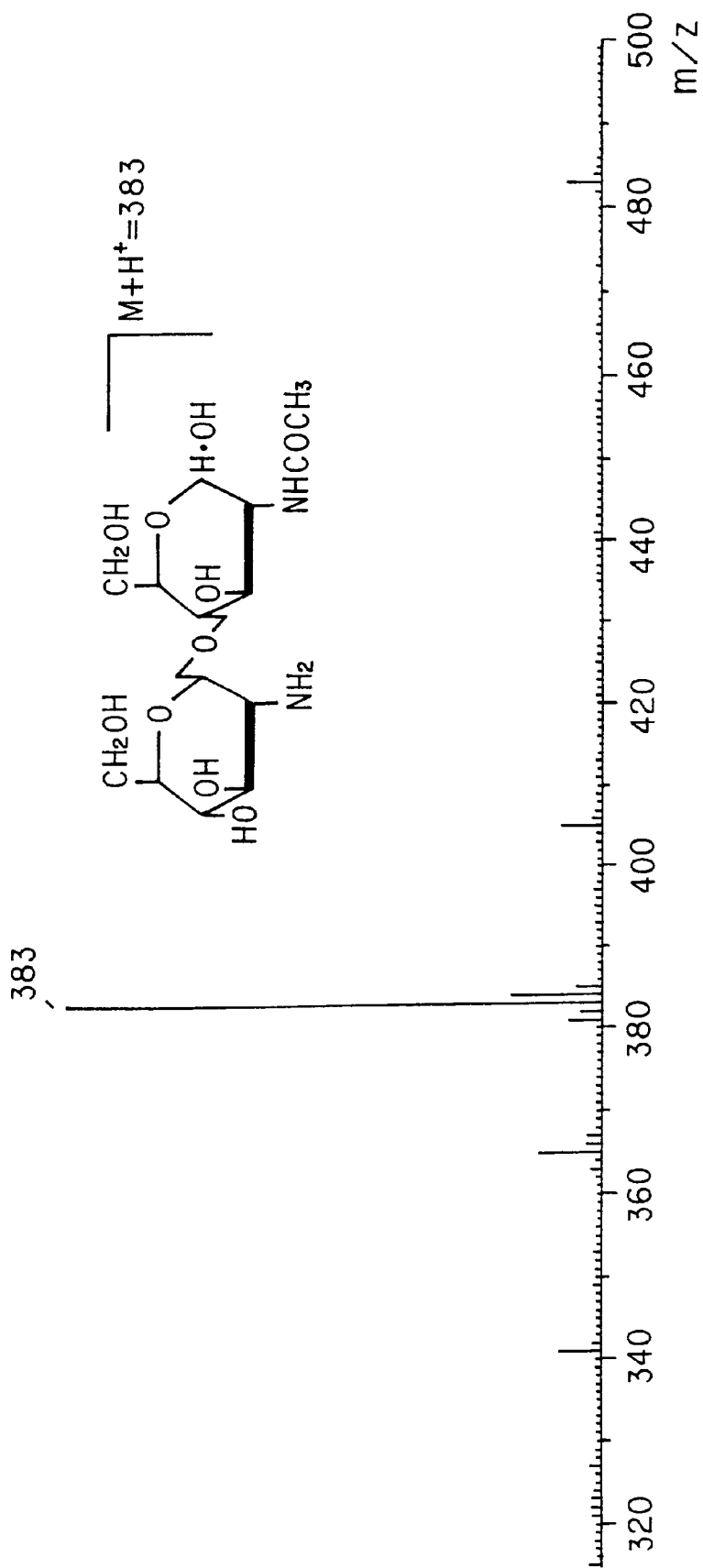
FIG. 1 is a mass spectrum of the compound of the invention.
Figure 2:
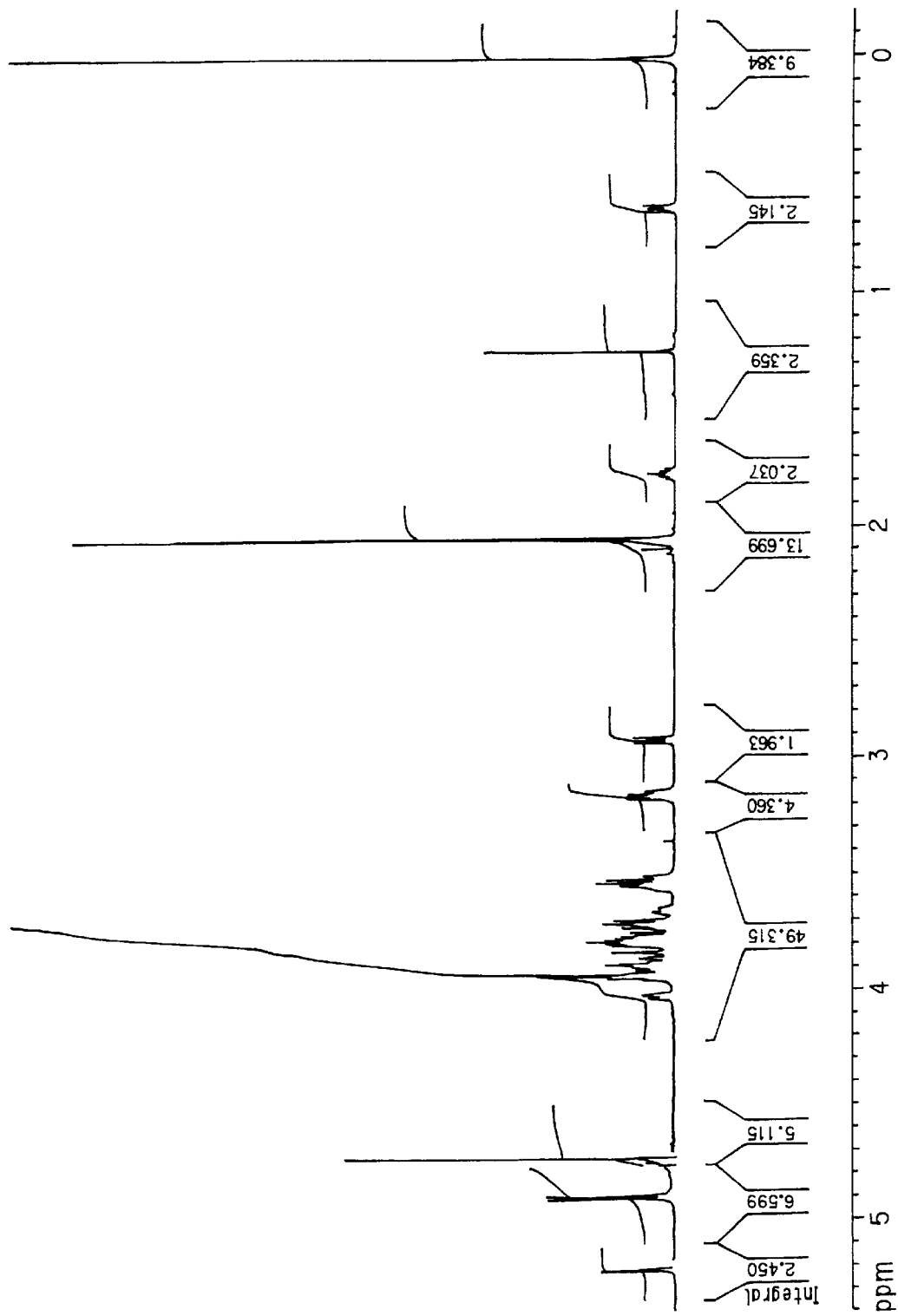
FIG. 2 is a $^1$H-NMR spectrum of the compound of the invention.
Figure 3A:
FIGS. 3A, 3B, 3C and 3D show the variation in the chromatographic patterns of different samples as sampled at predetermined intervals in the process of producing the compound of the invention, using di-N-acetylchitobiose as the substrate, in which the individual samples were analyzed through high-performance liquid chromatography.
Figure 3B:
Figure 3C:
Figure 3D:
Figure 4A:
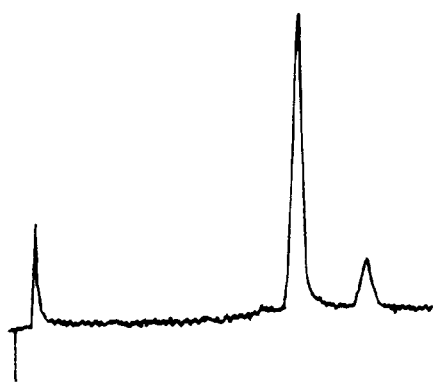
FIGS. 4A, 4B, 4C and 4D show the variation in the chromatographic patterns of different samples as sampled at predetermined intervals in the process of producing the compound of the invention, using di-N-acetylchitobiose as the substrate, in which the individual samples were analyzed through high-performance liquid chromatography.
Figure 4C:
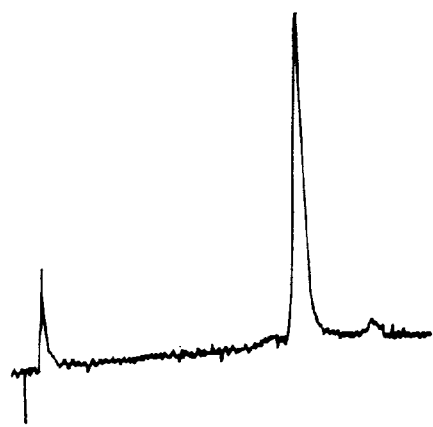
Figure 4B:
Figure 4D:

The structure of the compound obtained was analyzed through mass spectrography and nuclear magnetic resonance analysis of the compound. FIG. 1 is a mass spectrum of the compound, and FIG. 2 is a $^1$H-NMR spectrum of the same.

EXAMPLES

Now, the present invention is described in more detail with reference to the following Examples, which, however, are not intended to restrict the scope of the invention.

Example 1

(1) Purification of deacetylase

Colletotrichum lindemuthianum ATCC 56676 was inoculated into a medium comprising 0.28% glucose, 0.123% magnesium sulfate (7-hydrate), 0.2% proteose peptone, 0.272% potassium dihydrogenphosphate and 2.0% agar, and statically cultivated in the dark at 25° C. for 7 days to produce black cells.

Next, the cells were implanted into 200 ml of a medium (pH 5.8) comprising 1% malt extract, 0.4% yeast extract and 0.4% glucose and put in a 500-ml Erlenmeyer flask, and incubated in the dark at 22° C. with shaking at a revolution of 100 rpm for one minute. Around the 8th day, the cells began to secrete a substance having an enzymatic activity in the culture, and the enzymatic activity increased until the 18th day. After 18 days, the incubation was stopped, and the culture was filtered through a nylon filter and then passed through glass fibers to remove fine grains to recover the culture filtrate.

Ammonium sulfate was added to the filtrate at 4° C. to have a concentration of 80% saturation, then left statically as it was overnight, and thereafter centrifuged to recover the precipitate. This precipitate was dissolved in a small amount of 50 mM sodium tetraborate/HCl buffer (pH 8.5) and dialyzed against the same buffer. The resulting dialysate, crude enzyme liquid was fractionated and purified through hydrophobic chromatography and anion chromatography to obtain a chitin deacetylase. This enzyme gave a single band in SDS gel electrophoresis (see Japanese Patent Application Laid-Open No. 8-289785).

(2) Production of 2-acetylamino-4-O-(2-amino-2-deoxy-β-D-glucopyranosyl)-2-deoxy-D-glucose 0.40 mg of di-N-acetylchitobiose (manufactured by Seikagaku Kogyo KK) was dissolved in 0.2 ml of 20 mM sodium tetraborate/HCl buffer (pH 8.5), and 0.05 units of the imperfect fungus Colletotrichum lindemuthianum-derived, pure chitin deacetylase obtained in (1) was added thereto and reacted at 45° C. for 3 hours.

In this process, the reaction mixture was sampled at predetermined intervals and the individual samples were analyzed through ion chromatography using CarboPac PA-1 Column (manufactured by DIONEX Co.). The patterns obtained are shown in FIGS. 3A to 3D and FIGS. 4A to 4D. As in these, one reaction product was obtained as a result of this process, and the peak for this product in each pattern became higher from the initial stage of the reaction with the decrease in the substrate, di-N-acetylchitobiose. These patterns had few other peaks derived from any other compounds. Three hours after the start of the reaction, the peak derived from the starting substance, di-N-acetylchitobiose was not quantified at all by the detector.

As in the above, it is understood that the substrate was converted into the compound that gave a single peak, while being rapidly decreased.

Next, the reaction product was purified through a cation-exchange resin, Amberlite CG-120 (manufactured by Organo Co.), and then de-salted through electric dialysis. This was analyzed using a mass spectrometer (manufactured by JEOL Co.), which gave a signal of [M+H$^+$]=383. Thus, it was presumed that the compound produced herein has a molecular weight of 382. As a result of its $^1$H-NMR analysis, this compound was decided to have a structure of 2-acetylamino-4-O-(2-amino-2-deoxy-β-D-glucopyranosyl)-2-deoxy-D-glucose.

Example 2

20 mg of di-N-acetylchitobiose was dissolved in 10 ml of 20 mM sodium tetraborate/HCl buffer (pH 8.5), and 1.5 ml of an expansive resin, Q-Sepharose FF (manufactured by Pharmacia Co.) was suspended in the resulting solution. To this suspension was added 1.5 units of the pure chitin deacetylase obtained in Example 1(1), and reacted at 45° C. for 16 hours.

After the reaction, the Q-Sepharose resin was spontaneously precipitated, and the resulting transparent supernatant was recovered. A part of the supernatant was analyzed through ion chromatography using CarboPac PA-1 Column (produced by DIONEX Co.).

The pattern obtained had only the peak for 2-acetylamino-4-O-(2-amino-2-deoxy-β-D-glucopyranosyl)-2-deoxy-D-glucose but had no peak for the starting compound, di-N-acetylchitobiose.

Example 3

2-Acetylamino-4-O-(2-amino-2-deoxy-β-D-glucopyranosyl)-2-deoxy-D-glucose prepared in Example 1 was used as a substrate for measuring the enzymatic activity and was processed with 0.07 units of β-N-acetylhexosaminidase (derived from *Penicillum oxalicum*, manufactured by Seikagaku Kogyo KK) having an exo-type chitinase activity in 50 mM sodium citrate buffer (pH 4.5) at 37° C. for 1 hour, but the decomposition of the substrate was not observed.

On the other hand, when di-N-acetylchitobiose was processed with the same enzyme, it gave N-acetylglucosamine. This verified that this enzyme recognizes the N-acetyl group of the glucosamine residue positioned at the non-reducing terminal of the substrate, di-N-acetylchitobiose.

As has been mentioned in detail hereinabove with reference to its embodiments, the method of the present invention efficiently produces 2-acetylamino-4- O-(2-amino-2-deoxy-β-D-glucopyranosyl)-2-deoxy-D-glucose and its salts, starting from di-N-acetylchitobiose which is easily available in any desired amount. According to the method of the present invention, it is possible to stably produce said product. The product thus produced in the method of the invention has many applications in various fields. For example, it is usable as a substrate for measuring enzymatic activities, and also as a starting substance in the production of various food materials and in the field of glyco-chain engineering.

While the invention has been described in detail and with reference to specific embodiments thereof, it will be apparent to one skilled in the art that various changes and modifications can be made therein without departing from the spirit and scope thereof.

The entire disclosure of Japanese Patent Application No. 9-156092 filed on May 30, 1997 including specification, claims and summary are incorporated herein by reference in its entirety.

What is claimed is:

1. A method for producing 2-acetylamino-4-O-(2-amino-2-deoxy-β-D-glucopyranosyl)-2-deoxy-D-glucose of the following formula (I) and its acid-addition salts thereof,

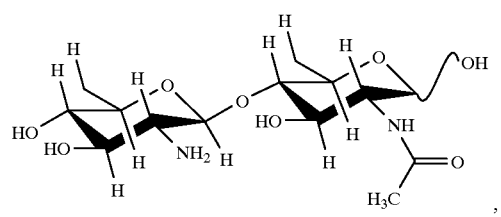

(I)

which comprises reacting di-N-acetylchitobiose with a microorganism-derived deacetylase, the deacetylase being *Colletotrichum lindemuthianum* ATCC 5667-derived chitin deacetylase.

2. The method of claim 1, wherein the acid-addition salts are selected from the group consisting of hydrochloride and acetate.

3. The method of claim 1, wherein the di-N-acetylchitobiose is dissolved in a sodium tetraborate/HCl buffer to prepare a solution having a substrate concentration of 0.1 to 0.5%.

4. The method of claim 3, wherein the pH of the solution is 8.5.

5. The method of claim 4, wherein the substrate concentration is 0.2%.

6. The method of claim 3, wherein the deacetylase is in an amount of 0.01 to 0.3 units.

7. The method of claim 1, wherein the deacetylase is in an amount of 0.05 units.

8. The method of claim 1, wherein the reacting is carried out at a temperature of 30 to 60° C.

9. The method of claim 1, wherein the reacting is carried out for 1 to 6 hours.

10. The method of claim 8, wherein the reacting is carried out for 2 to 4 hours.

11. The method of claim 9, wherein the reacting is carried out at a temperature of 45° C.

12. The method of claim 3, wherein the deacetylase is in an amount of 0.01 to 0.3 units, and the reacting is carried out at a temperature of 30 to 60° C. for 1 to 6 hours.

13. The method of claim 12, wherein the reacting is carried out for 2 to 4 hours.

14. The method of claim 13, wherein the reacting is carried out at a temperature of 45° C.

15. The method of claim 1, wherein the di-N-acetylchitobiose is dissolved in a sodium tetraborate/HCl buffer to prepare a solution having a substrate concentration of 0.1 to 0.5%; and the chitin deacetylase is in an amount of 0.01 to 0.3 units.

* * * * *